(12) United States Patent
Lin et al.

(10) Patent No.: US 8,372,634 B2
(45) Date of Patent: *Feb. 12, 2013

(54) STORAGE-ACCESS APPARATUS FOR STORING PRODUCTS AND STORAGE SYSTEM THEREOF

(75) Inventors: Shang-Chih Lin, Sanchong (TW); Jia-You Chen, Taipei (TW)

(73) Assignee: Healthbanks Biotech Co., Ltd., Taipei (TW)

( * ) Notice: Subject to any disclaimer, the term of this patent is extended or adjusted under 35 U.S.C. 154(b) by 1011 days.

This patent is subject to a terminal disclaimer.

(21) Appl. No.: 12/292,587

(22) Filed: Nov. 21, 2008

(65) Prior Publication Data

US 2009/0144494 A1 Jun. 4, 2009

(30) Foreign Application Priority Data

Nov. 23, 2007 (TW) .............................. 96144514 A

(51) Int. Cl.
*C12M 1/00* (2006.01)
*C12M 3/00* (2006.01)
*A47F 5/02* (2006.01)
*A47F 5/12* (2006.01)

(52) U.S. Cl. .............. 435/307.1; 435/303.1; 435/809; 62/378; 62/381; 211/163; 211/78; 211/70; 211/58; 211/49.1; 211/40; 211/41.12; 211/169; 211/169.1; 211/170; 211/144; 414/788; 414/27; 414/331.01; 414/331.02

(58) Field of Classification Search ............... 435/307.1, 435/303.1, 809, 378; 62/378, 381; 211/163, 211/78, 70, 58, 49.1, 40, 41.12, 169, 169.1, 211/170, 144; 414/788, 27, 331.01, 331.02
See application file for complete search history.

(56) References Cited

U.S. PATENT DOCUMENTS

| | | | | |
|---|---|---|---|---|
| 3,163,994 A | * | 1/1965 | Haumann et al. | 62/218 |
| 6,302,327 B1 | * | 10/2001 | Coelho et al. | 235/383 |
| 2004/0154322 A1 | * | 8/2004 | Felder et al. | 62/177 |
| 2006/0105450 A1 | * | 5/2006 | Owen | 435/303.3 |
| 2008/0092581 A1 | * | 4/2008 | Schumann et al. | 62/378 |

* cited by examiner

*Primary Examiner* — Nathan Bowers
(74) *Attorney, Agent, or Firm* — Bacon & Thomas, PLLC

(57) ABSTRACT

A storage-access apparatus includes a first support device including a first base; at least one first storage-access device and at least one first storage device, disposed on the first base and arranged in a first circle; a second support device including a second base; at least one second storage-access device and at least one second storage device, disposed on the second base and arranged in a second circle; and a transporting device, wherein the first storage-access device, the first storage device, the second storage-access device and the second storage device each has plural compartments, the transporting device corresponds to the compartments, and the first storage-access device and the first storage device can rotate relative to the second storage-access device and the second storage device. Accordingly, the storage-access apparatus can be employed in depositing and picking up products independently. Also disclosed is a storage system including, among others, the storage-access apparatus.

30 Claims, 11 Drawing Sheets

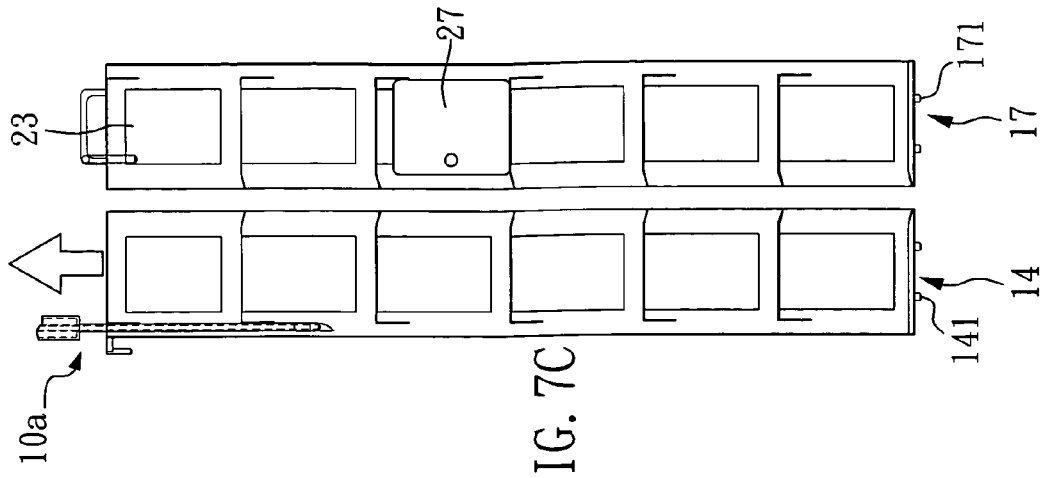
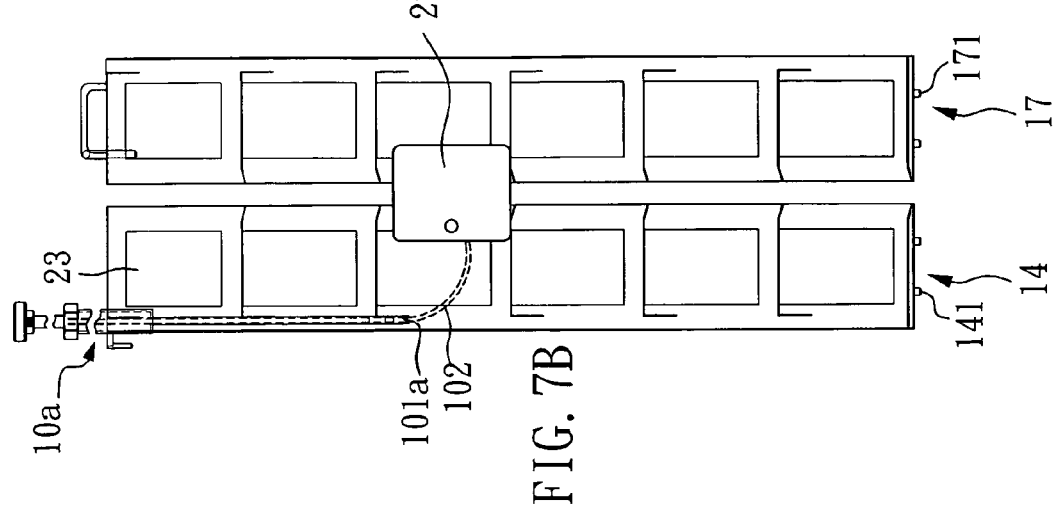
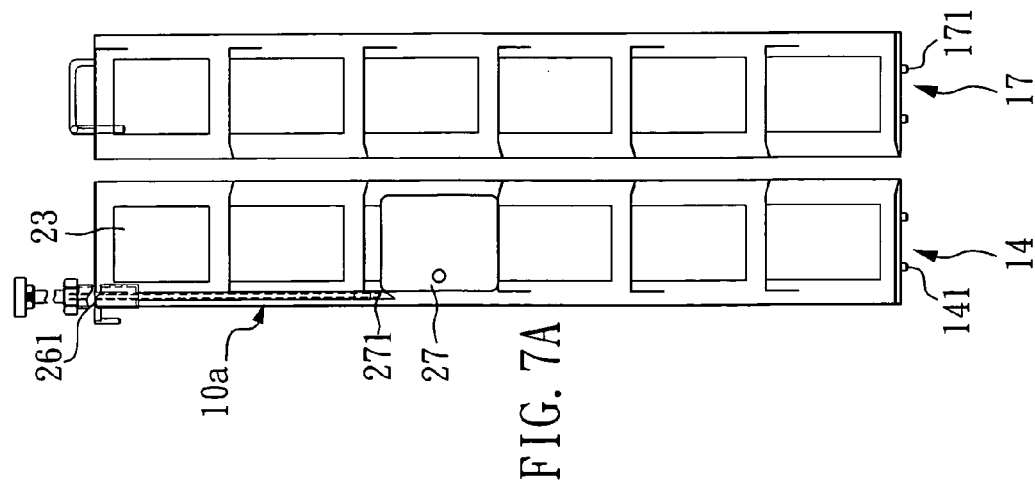

STORAGE-ACCESS APPARATUS FOR STORING PRODUCTS AND STORAGE SYSTEM THEREOF

BACKGROUND OF THE INVENTION

1. Field of the Invention

The present invention relates to a storage-access apparatus for storing products and a storage system thereof, and more particularly, to a storage-access apparatus and a storage system thereof run independently for storage-access operations and as such, lowering cost and raising storage-access accuracy can be achieved.

2. Description of Related Art

Currently, ultra-low temperature storage apparatuses are normally run under an ultra-low temperature environment (such as liquid nitrogen at −196° C.), mostly for storing biocells or body fluids, such as cord blood, bone marrow, placenta, embryo, sperm, and ovum. However, since the use of specimens for cord blood, bone marrow, placenta, embryo, sperm, or ovum is not considerably immediate, an ultra-low temperature storage apparatus for storing the specimens over a long period of time becomes necessary. Biotechnology has been developed rapidly in recent decades and in particular, because the cord blood contains abundant stem cells, it has been widely adopted in therapy. The issue of cord blood deposit has been receiving a lot of attention.

Nowadays, there are several kinds of storage tanks for being used by cord blood banks, for example, 1) conventional liquid nitrogen storage tanks (MVE, Tayler-Wharton); and 2) automatic mechanical storage tanks (TG BioArchieve System).

Conventionally, liquid nitrogen storage tanks relate to an open-lid type, where specimens contained in the storage tanks are stacked up in cartridges. To the effect, there are several cartridges contained in the storage tanks, whereas a plurality of specimens is stacked in the cartridges. Nevertheless, when an operator wishes to access to one of the specimens, other specimens frozen in the same cartridge will be taken out together. This would possibly affect activity of cells on the specimens because of temperature being changed abruptly. Moreover, since the liquid nitrogen storage tanks are of open-lid type, upon proceeding with storage and access actions, such a design of open-lid type will make moisture on surface of the liquid nitrogen become condensed. As a result, the labeling of specimens is concealed by condensation, and accuracy and speed of the storage and access are greatly affected.

The mechanical storage tank (BioArchieve System) relates to an automatic storage tank using hooks of robotic arms to hang the specimens on wall of the storage tank. Because the mechanical storage tank can perform the storage and access actions independently, the specimens at other storage positions would not be affected. In view of the fact that the BioArchieve System employs the hooking measure to store the specimens, the specimens may fall to bottom of the storage tank when the storage tank rocks and the specimens swing. Based on this ground, when the specimens are stored with this measure, the storage tank is, in principle, not allowed to be delivered or rocked in a great extent. Moreover, when the robotic arms are manipulated, moving upward or downward of the robotic arms will make moisture in the air permeate into joints of the robotic arms which are then frosted. The thus-impeded robotic arms, when manipulated, will produce relatively high frictional resistance, or even fail. Besides, the BioArchieve System relies on a computer for operation control, where electrical power is consumed, and after long-term use, precision electronic components may be damaged. In particular, the BioArchieve System is quite complex in design, and as such, high costs incurred in purchase and maintenance are the disadvantage.

SUMMARY OF THE INVENTION

To solve the problems mentioned above, the present invention is to provide a storage-access apparatus for storing a plurality of products, comprising a first support device including a first base; at least one first storage-access device which is supported on the first base and is provided for depositing and picking up the products; at least one first storage device which is supported on the first base and is provided for storing the products; a second support device including a second base; at least one second storage-access device which is supported on the second base and is provided for depositing and picking up the products; at least one second storage device which is supported on the second base and is provided for storing the products; and a transporting device which is provided for transferring the products. The first storage-access device, the first storage device, the second storage-access device, and the second storage device each has a plurality of compartments for receiving the products; and the transporting device is provided for transferring the products in the compartments. The first storage-access device and the first storage device are arranged in a first circle, while the second storage-access device and the second storage device are arranged in a second circle. The first storage-access device and the first storage device can rotate relative to the second storage-access device and the second storage device.

According to the present invention, the storage-recess apparatus is designed to have a circular arrangement structure so as to achieve the purpose of independent storage and access. In addition, the storage-recess apparatus according to the present invention is not limited to have a two-circle structure. If necessary, the storage-recess apparatus, based on the same principle of design, may have other multiple-circle structures, for instance, a four-circle structure.

In the present invention, the first storage-access device and the second storage-access device are movable and are provided for picking up or depositing the products, whereas the first storage device and the second storage device are provided for storing the products. In detail, when proceeding with a pickup, the products stored in the first storage device can be transferred, by the transporting device, to the second storage-access device; or the products stored in the second storage device be transferred to the first storage-access device. Thereafter, to complete a pickup action by picking up the products in the first or second storage-access devices, and vice versa, a storage action can be completed.

According to the present invention, the compartments are separated from one another by a plurality of partitions which are curved at edges so as to facilitate smooth transfer of the products. The first storage-access device, the first storage device, the second storage-access device, and the second storage device are each provided with an open side and, oppositely, a closed side. The open sides of the first storage-access device and the first storage device face toward the open sides of the second storage-access device and the second storage device, such that the products can be transferred in the storage-access apparatus. The closed sides can prevent the products from falling.

Further, the transporting device can be designed as a mechanism able to transfer the products in the compartments. Preferably, the transporting device refers to a plurality of push-rod units each including a casing having a leading piece and an elastic element disposed in the casing and extending out of the leading piece and into various depths of the compartments.

The first storage-access device, the first storage device, the second storage-access device, and the second storage device are each provided, at its closed side, with a through first guiding portion, such that the push-rod unit can be put into the first guiding portion for transferring the products in the compartments.

The storage-access apparatus according to the present invention may further comprise a partition element corresponding to the open sides of the first storage-access device, the first storage device, the second storage-access device, and the second storage device. The partition element is not limited to any specific configuration so long as the purpose of preventing the products from falling out of the compartments, due to rocking of the storage-access apparatus, can be achieved. Preferably, the partition element refers to a partition rod, and when moving the storage-access apparatus according to the present invention, the partition rod can be inserted into a through second guiding portion provided at the open side of each of the first storage-access device, the first storage device, the second storage-access device, and the second storage device so as to prevent the products from falling out due to rocking of the storage-access apparatus.

The first support device may further include a rotating unit connected with the first storage-access device and the first storage device. The first storage-access device and the first storage device are positioned between the rotating unit and the first base. The first storage-access device and the first storage device can, through the rotating unit, rotate relative to the second storage-access device and the second storage device. The rotating unit is disposed at the top or bottom of the storage-access apparatus, preferably at the top of the apparatus so as to facilitate maintenance therefor.

Further, in the storage-access apparatus according to the present invention, the first base has a plurality of first positioning portions, corresponding to locations of the first storage-access device and the first storage device, for anchoring bottoms of the first storage-access device and the first storage device. Similarly, the second base has a plurality of second positioning portions, corresponding to locations of the second storage-access device and the second storage device, for anchoring bottoms of the second storage-access device and the second storage device. The first and second positioning portions can be designed as any structure having effectiveness of positioning, such as slots, holes, and so forth. Preferably, the first and second positioning portions can be a hole-like structure so as to lower manufacturing cost and to reduce manufacturing processing.

The rotating unit of the first support device includes a bearing disk, a first rotating element, and a second rotating element, wherein the bearing disk are fixed to the second base, the first rotating element rotates relative to the bearing disk, and the second rotating element is connected with the first rotating element.

Rotation of the rotating unit can be controlled manually or by a step motor, wherein the second rotating element is provided with a handle for controlling rotation thereof.

The rotating unit may further include a plurality of first rods connected with the second rotating element and the first base so as to reinforce the connecting relationship between the rotating unit and the first base, such that the first base can be rotated along with the rotating unit.

Still further, the rotating unit may include at least one first guiding element which is connected with the second rotating element, and which corresponds to a location of the at least one first storage-access device, so that the first storage-access device, upon insertion thereinto, can be guided to an accurate position. Preferably, the first guiding element is connected with the first base.

In the present invention, the rotating unit may include a plurality of rolling elements, such as steel balls, interposed between the bearing disk and the first rotating element. When the first rotating element is rotated, it will rotate together with the rolling elements. In detail, the bearing disk may be provided with a plurality of holes for positioning the rolling elements, whereas the first rotating element may be provided with recesses corresponding to the rolling elements so as to restrict movement of the rolling elements, such that the rolling elements can be positioned in the recesses and facilitate rotation of the first rotating element.

Further, the rotating unit may include a plurality of positioning elements interposed between the bearing disk and the first rotating element, so that the first rotating element can reach to a target position while the first rotating element stops rotating. In detail, the bearing disk is locked with the plural positioning elements, and that the first rotating element is provided with a plurality of positioning holes corresponding to the positioning elements. As such, a combination of the positioning elements and the positioning holes can provide resistance, so that the first rotating element may not rotate too fast, and that when it stops rotating, the first storage-access device and the first storage device can accurately align with the second storage-access device and the second storage device.

According to the present invention, the second support device further includes a supporting unit which is fixed to the second base, where the second storage-access device and the second storage device are interposed between the supporting unit and the second base, such that the second storage-access device and the second storage device can be firmly supported on the second base. The supporting unit includes at least one second guiding element which corresponds to the location on which the at least one second storage-access device is disposed, so that the at least one second storage-access device can be guided and accurately inserted thereinto. Preferably, the second guiding element is connected with bottom of the second base.

The storage-access apparatus, according to the present invention, may further include a cover plate which covers the top of the apparatus so as to prevent temperature loss or invasion of foreign matter, in particular can prevent the apparatus from being effected by surface moisture, so that operators can carry out the access-storage job accurately. Further, according to the present invention, the cover plate can be of any materials having an anti-fogging feature, preferably, the cover plate refers to an acrylic plate or high-strength glass. In addition, the cover plate can be affixed with a label so as to help the operator assure accuracy of positioning.

Still further, the storage-access apparatus according to the present invention may comprise a plurality of cartridges for containing the products, such as specimens, where the cartridges are arranged in the compartments. The cartridges can store any type of products, and that the shapes of the cartridges are not to be limited so long as the cartridges can be moved among the compartments conveniently. The cartridges can be curved at edges so as to facilitate the cartridges to smoothly enter the compartments.

The cartridges are each provided, on surface, with an identification label, preferably, the identification label faces the first guiding portion, such that an optical-fiber lens or barcode reader can see through the first guiding portion and recognize image of the identification label.

According to the present invention, a storage system is further provided for storing a plurality of products, where the storage system comprises a storage tank filled with a liquid, and a storage-access apparatus, as mentioned above, which is disposed in the storage tank. According to the present invention, the storage tank can keep the liquid under a certain temperature suitable for storing the products. In the present invention, the liquid may be of low temperature liquid nitrogen. As such, the storage system, according to the present invention, can be used for storing specimens, such as stem cells.

The storage system, according to the present invention, can further comprise a defroster for removing frost from the storage tank so as to prevent the storage system from failure resulting from frosting.

Still further, the storage system can be electrically connected with a monitoring system so as to achieve the purpose of safety-and-function monitor. In the present invention, the monitor system is not to be limited, but may be a Positioning Bearing Vibration Spectrum Analysis Monitoring System, Storage Tank Liquid Level Monitoring System, Storage Tank Horizontal and Exterior Impact Monitoring System, Storage Tank Liquid Nitrogen Automatic Filling Monitoring System, Storage Tank Bottom Icing and Foreign Matters Monitoring System, Storage Tank Bio-pollution Monitoring System, Storage Tank Liquid Nitrogen Vaporization or Leakage Monitoring System, or various Sensors Detecting Signal Net Monitoring System (with, for instance, messaging and telephone monitor and warning functions), and so forth.

According to the present invention, since the storage-access apparatus and the storage system relate to manual manipulation mechanism, system shutdown due to electric power failure or robotic fault can be avoided. In addition, since the mechanism is relatively simple, manufacturing cost and maintenance difficulty can be lowered. Further, the transmission principle applied in the present invention can perform the storage and access actions independently, so that the specimens not to be accessed remain at the original position, and that loss of cell activity on the specimens due to abrupt temperature change can be avoided. Besides, in the present invention, the cover plate can perform an anti-fog effect so as to avoid the problem of visual blur due to condensation of moisture above the liquid nitrogen, and that accuracy and speed of access and storage can be enhanced.

Other objects, advantages, and novel features of the present invention will become more apparent from the following detailed description when taken in conjunction with the accompanying drawings.

BRIEF DESCRIPTION OF THE DRAWINGS

FIGS. 7A to 7C are perspective views illustrating actions of access and storage of the storage-access apparatus according to the present invention;

DETAILED DESCRIPTION OF THE PREFERRED EMBODIMENTS

Figure 1:
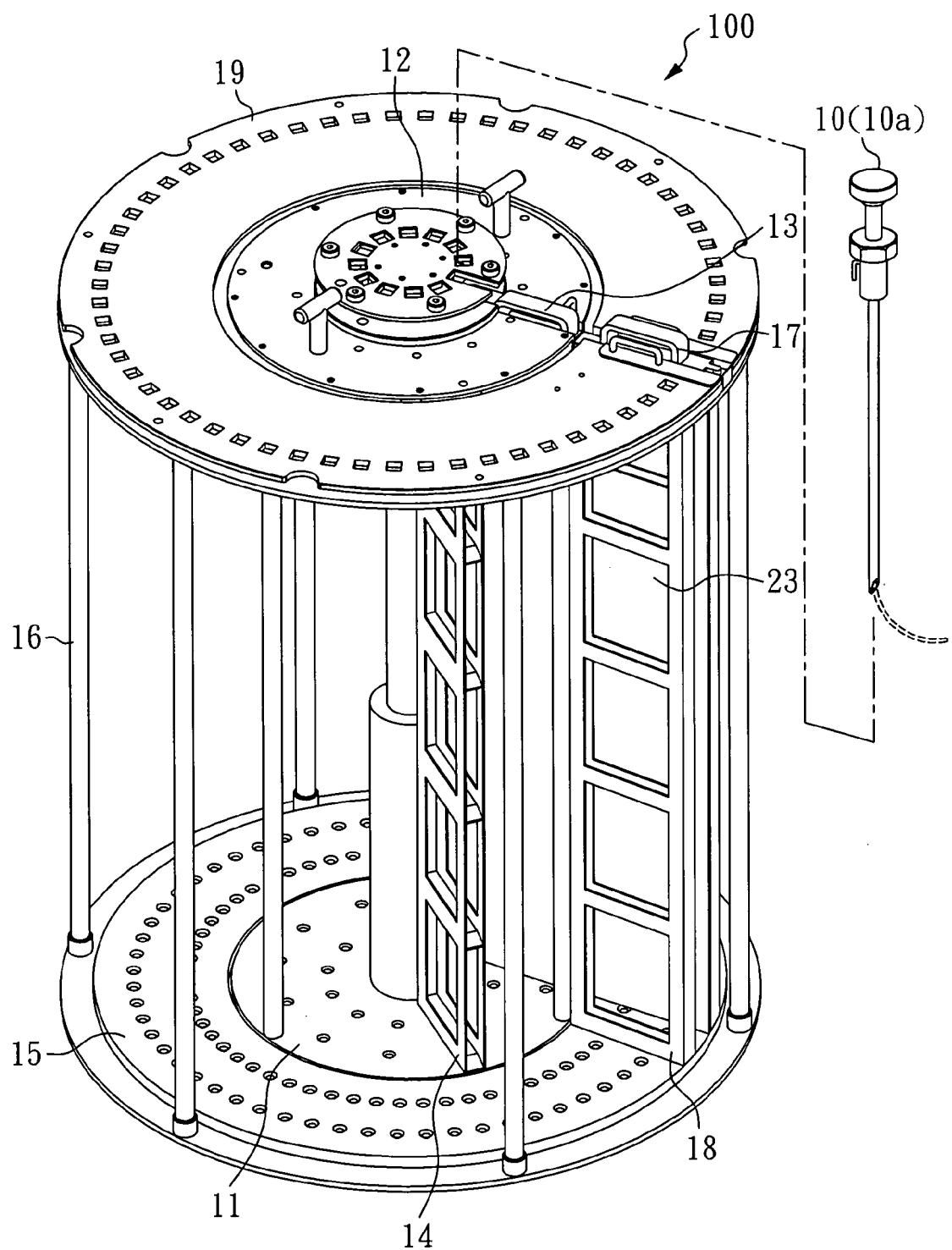
FIG. 1 is a perspective view, with parts removed, illustrating a storage-access apparatus according to the present invention.

Referring to FIG. 1, a perspective view illustrating a storage-access apparatus according to the present invention, the storage-access apparatus 100 comprises a first support device including a first base 11 and a rotating unit 12; at least one first storage-access device 13 and at least one first storage device 14 which are supported on the first base 11 and are arranged in a first circle; a second support device including a second base 15 and a supporting unit 16; at least one second storage-access device 17 and at least one second storage device 18 which are supported on the second base 15 and are arranged in a second circle; a cover plate 19 for covering the top of the storage-access apparatus 100; and a transporting device 10, wherein the first storage-access device 13, the first storage device 14, the second storage-access device 17, and the second storage device 18 each has a plurality of compartments 23, and the transporting device 10 is used for transferring products in each of the compartments 23, and the first storage-access device 13 and the first storage device 14 can rotate relative to the second storage-access device 17 and the second storage device 18.

According to the present invention, the rotating unit 12 is disposed at the top of the storage-access apparatus 100, and is connected with the first storage-access device 13 and the first storage device 14. The supporting unit 16 is fixed to the second base 15, and is connected with the second storage-access device 17 and the second storage device 18. The second storage-access device 17 and the second storage device 18 are located between the supporting unit 16 and the second base 15. The first storage-access device 13 and the first storage device 14 can, through the rotating unit 12, rotate relative to the second storage-access device 17 and the second storage device 18. With the help of the movable first storage-access device 13 and the first storage device 14, actions of storage and access for the storage-access apparatus 100, according to the present invention, can be performed without effecting unused products deposited in the first storage-access device 13 and the first storage device 14 so as to avoid damage to activity of organisms due to inappropriate temperature increase. Further, because the rotating unit 12, which has a complex design, is disposed at the top of the storage-access apparatus 100, maintenance for the apparatus can be undertaken easily. In addition, the cover plate 19, which covers the top of the apparatus, can prevent temperature loss or invasion of foreign matters, in particular can prevent the apparatus from being effected by fogging, so that operators can carry out the access-storage job accurately. Further, according to the present invention, the transporting device 10 refers to a plurality of push-rod units 10*a* (only one push-rod unit is shown), where each push-rod unit 10*a* can reach to the compartments 23 of various locations so as to access the products in the compartments 23.

Figure 2:
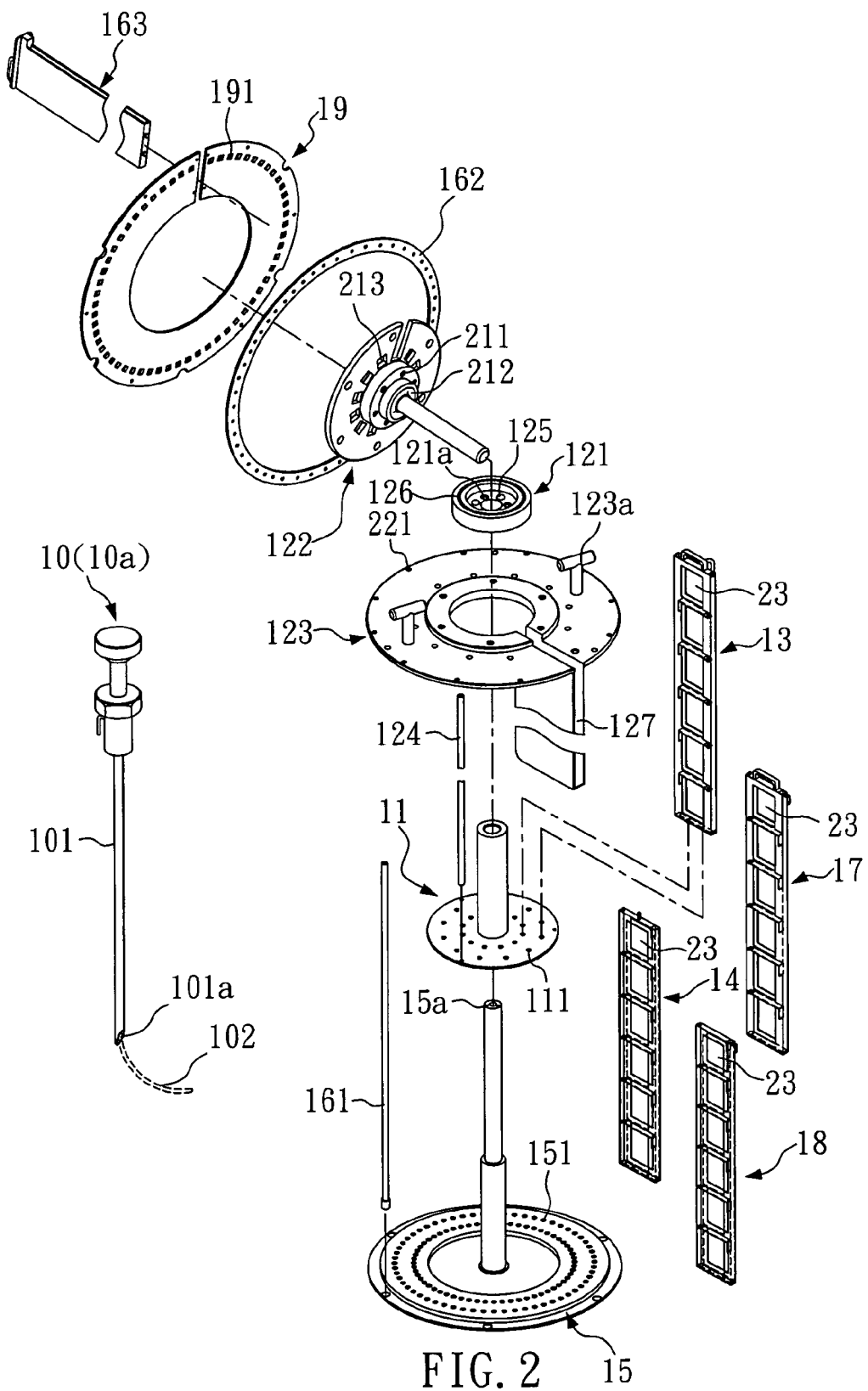
FIG. 2 is an exploded view illustrating the storage-access apparatus according to the present invention.
Figure 5A:
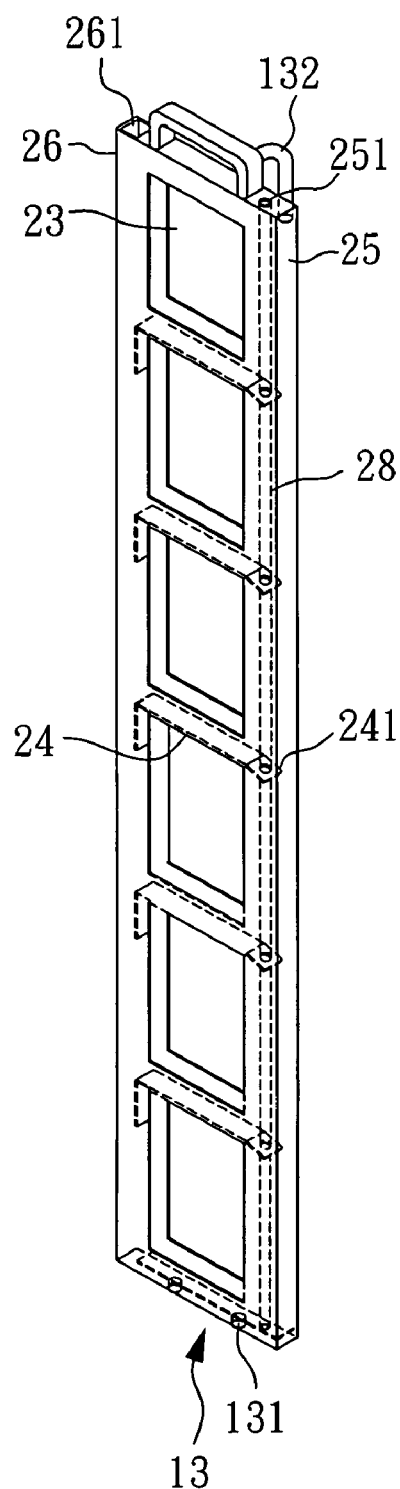
FIG. 5A is a perspective view illustrating a first storage-access device of the storage-access apparatus according to the present invention.
Figure 5B:
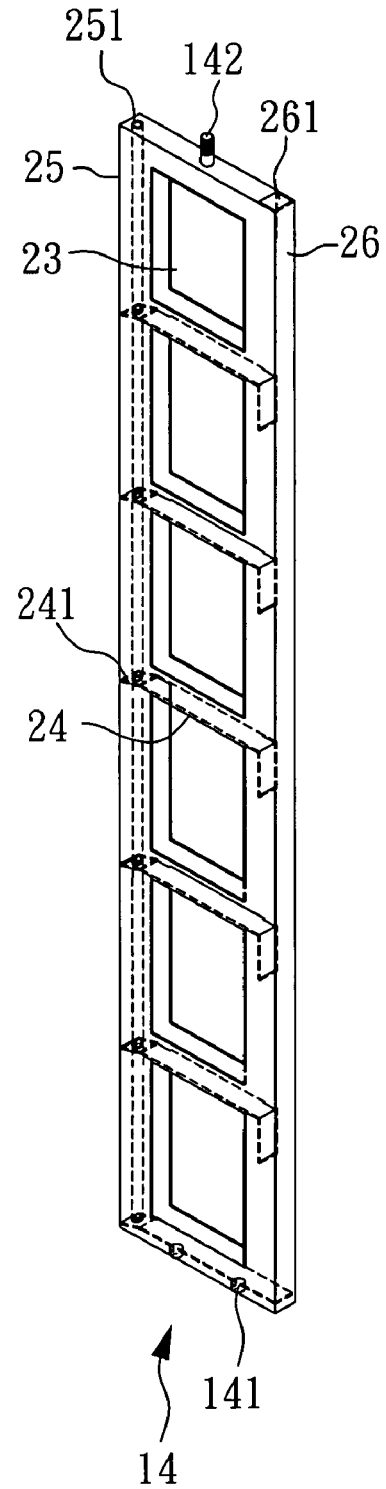
FIG. 5B is a perspective view illustrating a first storage device of the storage-access apparatus according to the present invention.

Referring to FIG. 2, an exploded view illustrating the storage-access apparatus according to the present invention, the structure and combination of elements of the storage-access apparatus 100 are detailed as follows:

As shown in FIG. 2, in the first support device, the first base 11 has a plurality of first positioning portions 111, corresponding to locations of the first storage-access device 13 and the first storage device 14, for anchoring bottoms of the first storage-access device 13 and the first storage device 14. In the present invention, the first positioning portions 111 refer to holes, such that protrusions 131, 141 underneath the first storage-access device 13 and the first storage device 14, as shown in FIGS. 5A and 5B, can be inserted into the first positioning portions 111.

Figure 3:
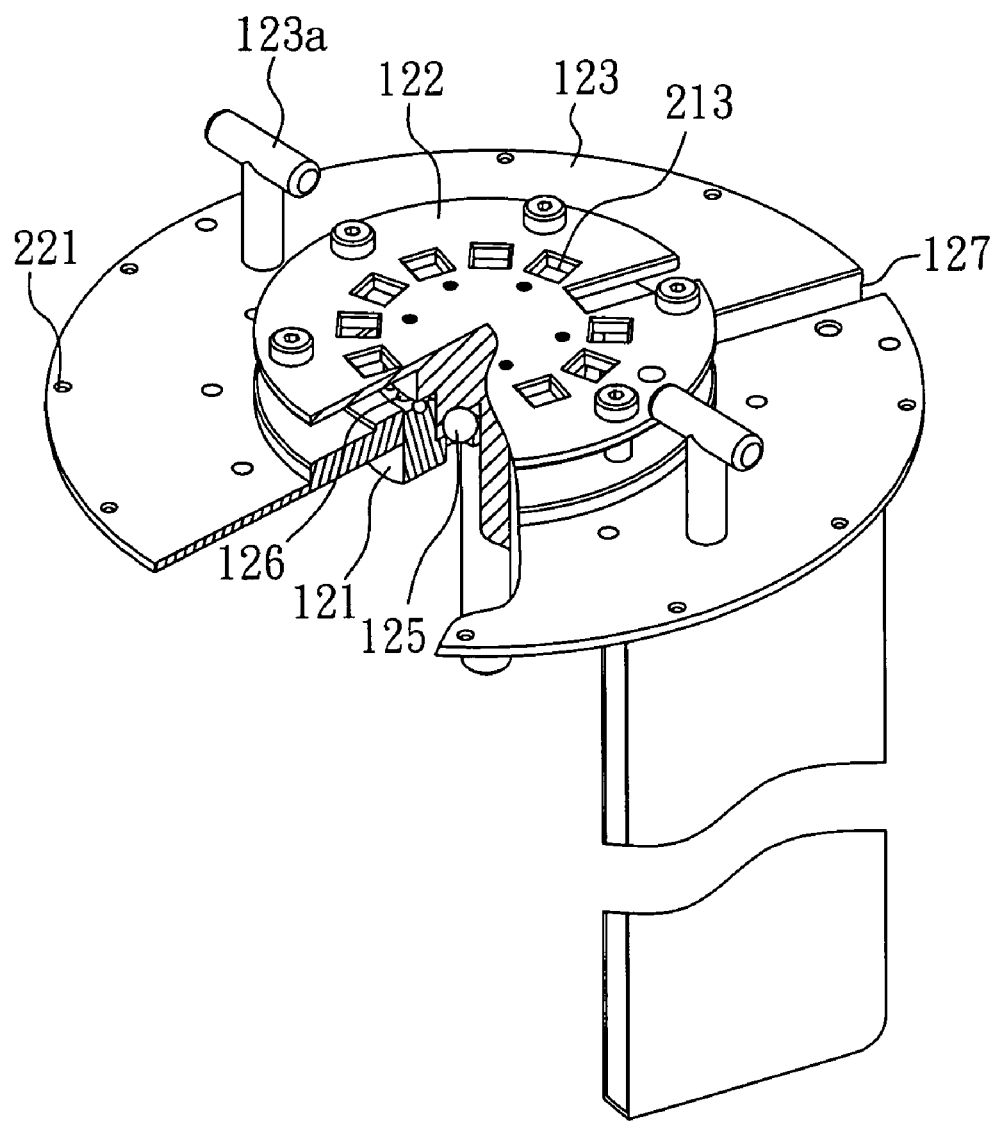
FIG. 3 is a perspective view, partly cut away, illustrating assembly of a bearing disk, a first rotating element, and a second rotating element of the storage-access apparatus according to the present invention.
Figure 4:
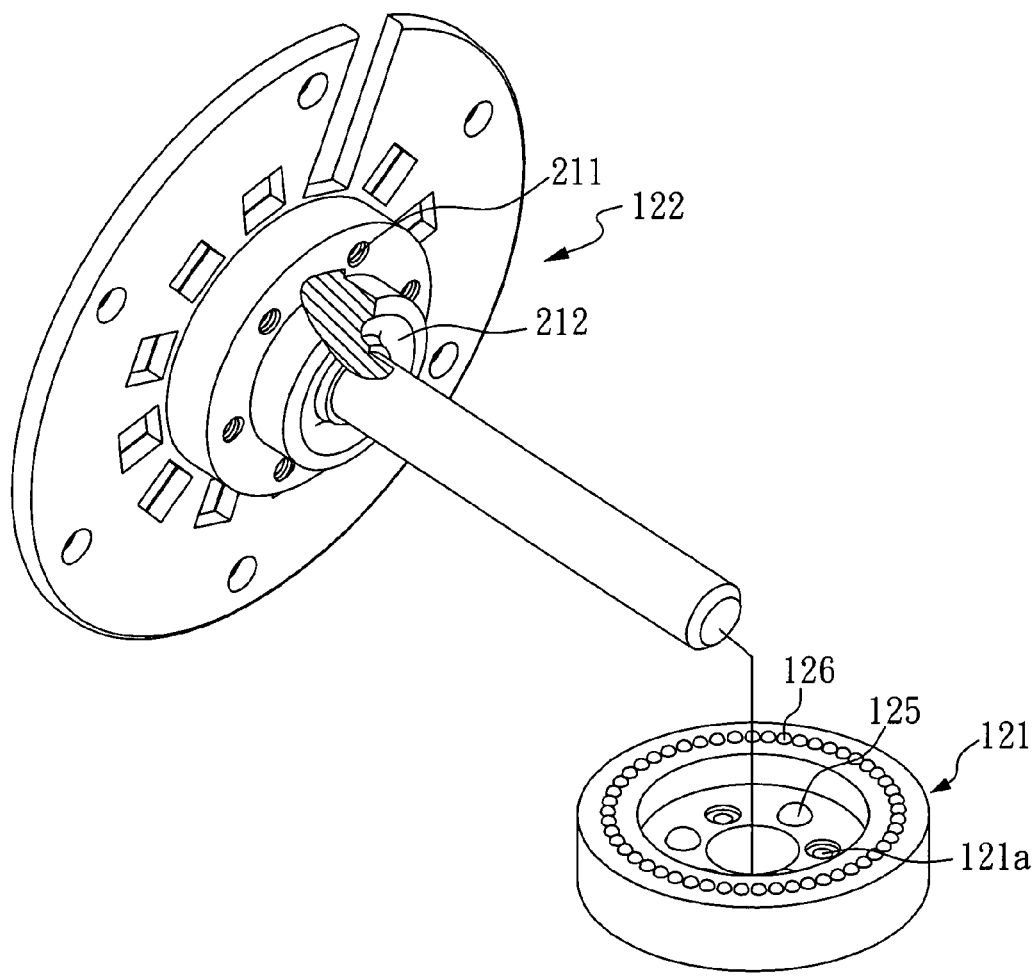
FIG. 4 is a perspective view illustrating the bearing disk and the first rotating element of the storage-access apparatus according to the present invention.

The rotating unit 12 of the first support device includes a bearing disk 121, a first rotating element 122, a second rotating element 123, a plurality of first rods 124, a plurality of rolling elements 125, a plurality of positioning elements 126, and a first guiding element 127. The first rods 124 are connected with the second rotating element 123 and the first base 11, and that the first guiding element 127 is connected with the second rotating element 123 and with the bottom of the first base 11, and corresponds to the location of the first storage-access device 13, so that the first storage-access device 13 can be disposed aligning with the location. As shown in FIG. 3, the first rotating element 122 rotates relative to the bearing disk 121, and that the second rotating element 123 is connected with the first rotating element 122. The second rotating element 123 is provided with a handle 123*a* for controlling rotation thereof. In detail, as shown in FIG. 4, a plurality of rolling elements 125 (in the present invention, the rolling elements refer to steel balls) is disposed in holes (not shown) of the bearing disk 121, and that the first rotating element 122 is provided with a recess 212 corresponding to the rolling elements 125. Further, the bearing disk 121 is locked with a plurality of positioning elements 126 (in the present invention, the positioning elements refer to steel balls), and that the first rotating element 122 is provided with a plurality of positioning holes 211 corresponding to the positioning elements 126. As such, when the first rotating element 122 is rotated, it will rotate together with the rolling elements 125, making the first rotating element 122 rotate smoothly, while the positioning elements 126, which correspond to the positioning holes 211, can provide resistance, so that the first rotating element 122 may not rotate too fast, and that when rotating is stopped, the first rotating element 122 can reach to a desirable position. This will achieve the purpose of rotational positioning.

Figure 5C:
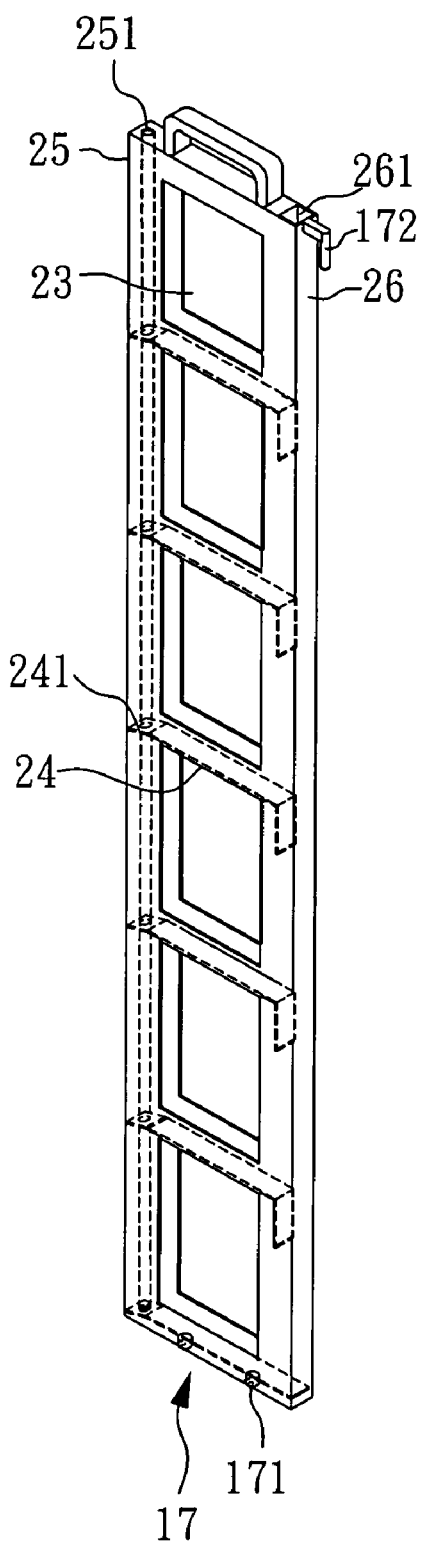
FIG. 5C is a perspective view illustrating a second storage-access device of the storage-access apparatus according to the present invention.
Figure 5D:
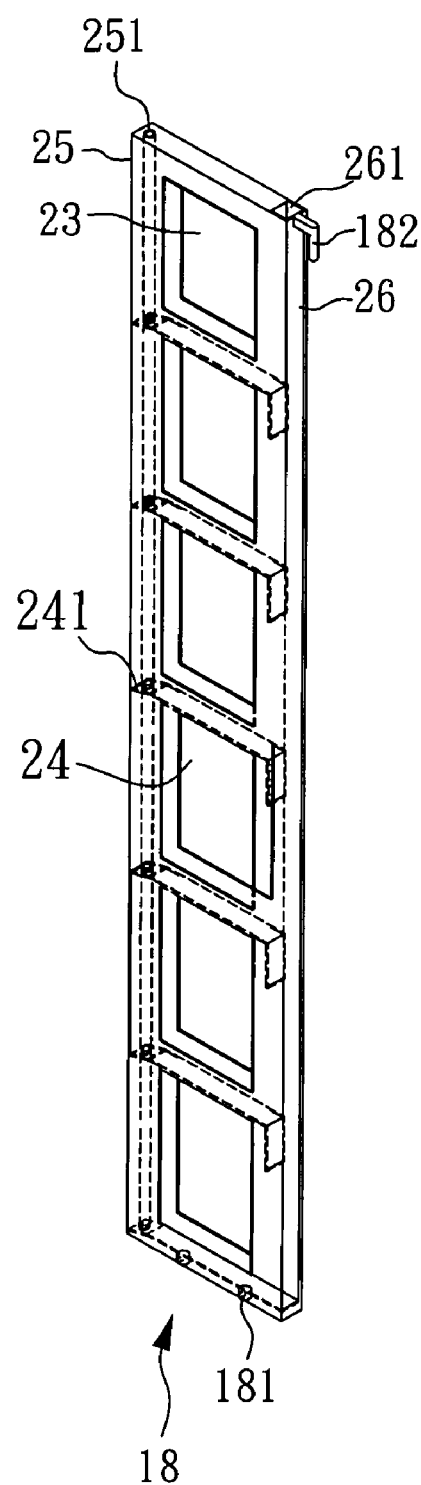
FIG. 5D is a perspective view illustrating a second storage device of the storage-access apparatus according to the present invention.

As shown in FIG. 2, in the second support device, the second base 15 has a plurality of second positioning portions 151, corresponding to locations of the second storage-access device 17 and the second storage device 18, for anchoring bottoms of the second storage-access device 17 and the second storage device 18. In the present invention, the second positioning portions 151 refer to holes, such that protrusions 171, 181 underneath the second storage-access device 17 and the second storage device 18, as shown in FIGS. 5C and 5D, can be inserted into the second positioning portions 151. Further, a locking portion 15*a* of the second base 15 is engaged with a locking portion 121*a* of the bearing disk 121 so as to secure the bearing disk 121.

The supporting unit 16 of the second support device has a plurality of second posts 161, a cover 162, and at least one second guiding element 163 which corresponds to the location on which the at least one second storage-access device 17 is disposed, so that the second storage-access device 17 can be guided and accurately inserted thereinto. The cover 162 is connected with the second posts 161, and that the second guiding element 163 is connected with the cover plate 19, the cover 162, and the second base 15, as shown in FIG. 1.

Further, the transporting device 10, as mentioned above, refers to a plurality of push-rod units 10*a* (only one push-rod unit is shown), where the push-rod unit 10*a* includes a casing 101 having a leading piece 101*a* and an elastic element 102 disposed in the casing 101 and extending out of the leading piece 101 and toward the compartments 23. The elastic element 102 of each push-rod unit 10*a* has a certain different amount of extension so as to extend, correspondingly, into various depths of the compartments 23.

Still further, as mentioned above, the first storage-access device 13, the first storage device 14, the second storage-access device 17, and the second storage device 18 each has a plurality of compartments 23. The compartments 23 in the first storage-access device 13 and the first storage device 14 correspond to the compartments 23 in the second storage-access device 17 and the second storage device 18, so that the products in the first storage-access device 13, the first storage device 14, the second storage-access device 17, and the second storage device 18 can be transferred to one another. In detail, as shown in FIGS. 5A to 5D, the compartments 23 are separated from one another by a plurality of partitions 24 which are curved at edges 241 so as to facilitate smooth transfer of the products. The first storage-access device 13, the first storage device 14, the second storage-access device 17, and the second storage device 18 are each provided with an open side 25 and, oppositely, a closed side 26. The closed side 26 has a first guiding portion 261 therethrough, and similarly, the open side 25 has a through second guiding portion 251. When moving the storage-access apparatus according to the present invention, a partition element 28 (in the present invention, the partition element refers to a partition rod) is provided so as to prevent the products from falling out due to rocking of the storage-access apparatus.

Figure 6:
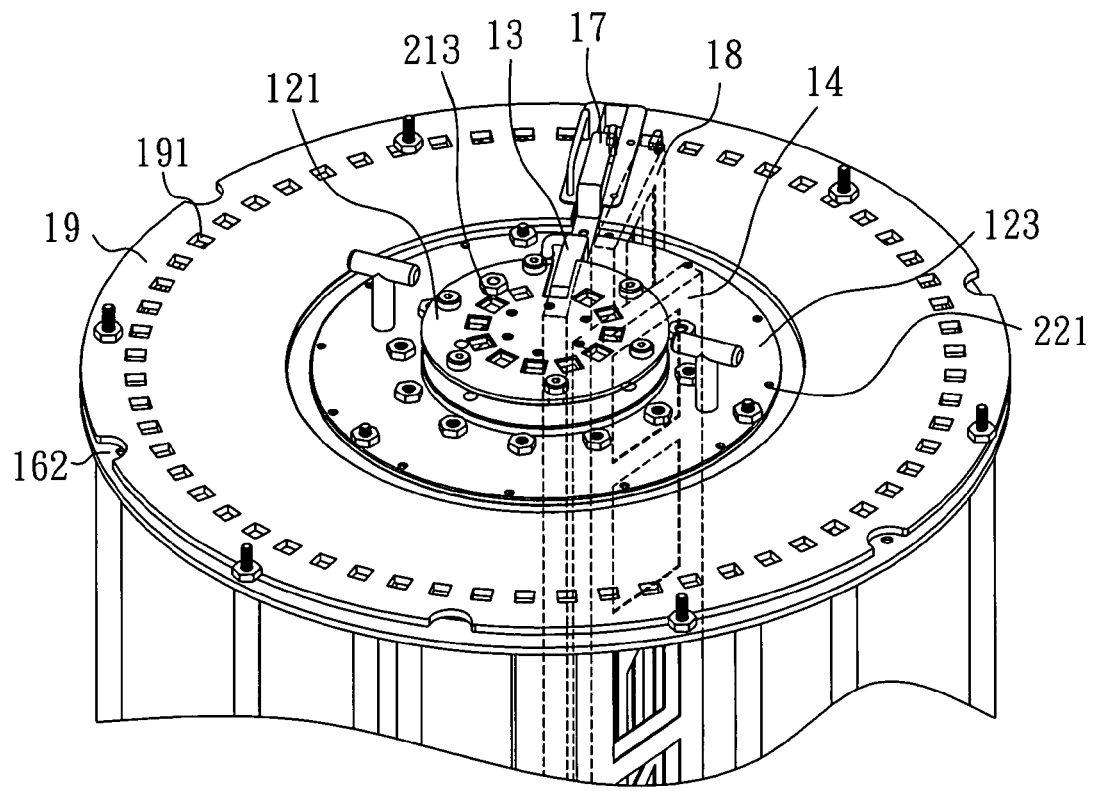
FIG. 6 is a perspective view illustrating the top of the storage-access apparatus according to the present invention.

As shown in FIGS. 5A to 5D, the first storage-access device 13, the first storage device 14, the second storage-access device 17, and the second storage device 18 are provided with hooks 132, 142, 172, and 182, respectively, so as to be engaged with the cover 162 of the second rotating element 123, as shown in FIG. 6.

As shown in FIG. 6, the first storage-access device 13 is disposed in the first guiding element 127, and that the first storage device 14 is attached to the second rotating element 123, where the plural first storage devices 14 are arranged in a first circular portion (only one first storage device 14 is shown). The second storage-access device 17 is disposed in the second guiding element 163, and that the second storage device 18 is attached to the cover 162 of the supporting unit 16, where the plural second storage devices 18 are arranged in a second circular portion (only one second storage device 18 is shown). The open side 25 of the first storage-access device 13 and of the first storage device 14 face toward the second circular portion, while the open side 25 of the second storage-access device 17 and of the second storage device 18 face toward the first circular portion, so that actions of access and storage can be performed. Further, the first rotating element 122 and the cover plate 19 are each provided with a plurality of first openings 213 and 191, respectively, so as to reveal, correspondingly, the first guiding portions 261. The second rotating element 123 is provided with a plurality of second openings 221 so as to reveal, correspondingly, the second guiding portions 251 of the first storage-access devices 13 and of the first storage devices 14.

Referring to FIGS. 7A to 7C, perspective views illustrating actions of access and storage of the storage-access apparatus according to the present invention, in the storage-access apparatus according to the present invention, the push-rod units 10a are put into the first guiding portions 261 so as to proceed with the actions of transfer. Suppose the second storage-access device 17 is used for an action of access, the push-rod unit 10a is first put into the first guiding portion 261 of the first storage device 14, then the top of the push-rod unit 10a is pressed down such that the elastic element 102 of the push-rod unit 10a extends out of the leading piece 101, and that the elastic element 102, which has a certain amount of extension, extends toward the compartment 23 in which a cartridge 27 is provided, so as to transfer the cartridge 27 to the compartment 23 of the second storage-access device 17, as shown in FIG. 7B. Thereafter, the elastic element 102 recovers to its original length and is received inside of the push-rod unit 10a, as shown in FIG. 7C. On the contrary, the actions shown from FIGS. 7C to 7A relate to storage of the products. Similarly, the first storage-access device 13 can be proceeded with actions for access or storage shown in FIGS. 7A to 7C.

Figure 8:
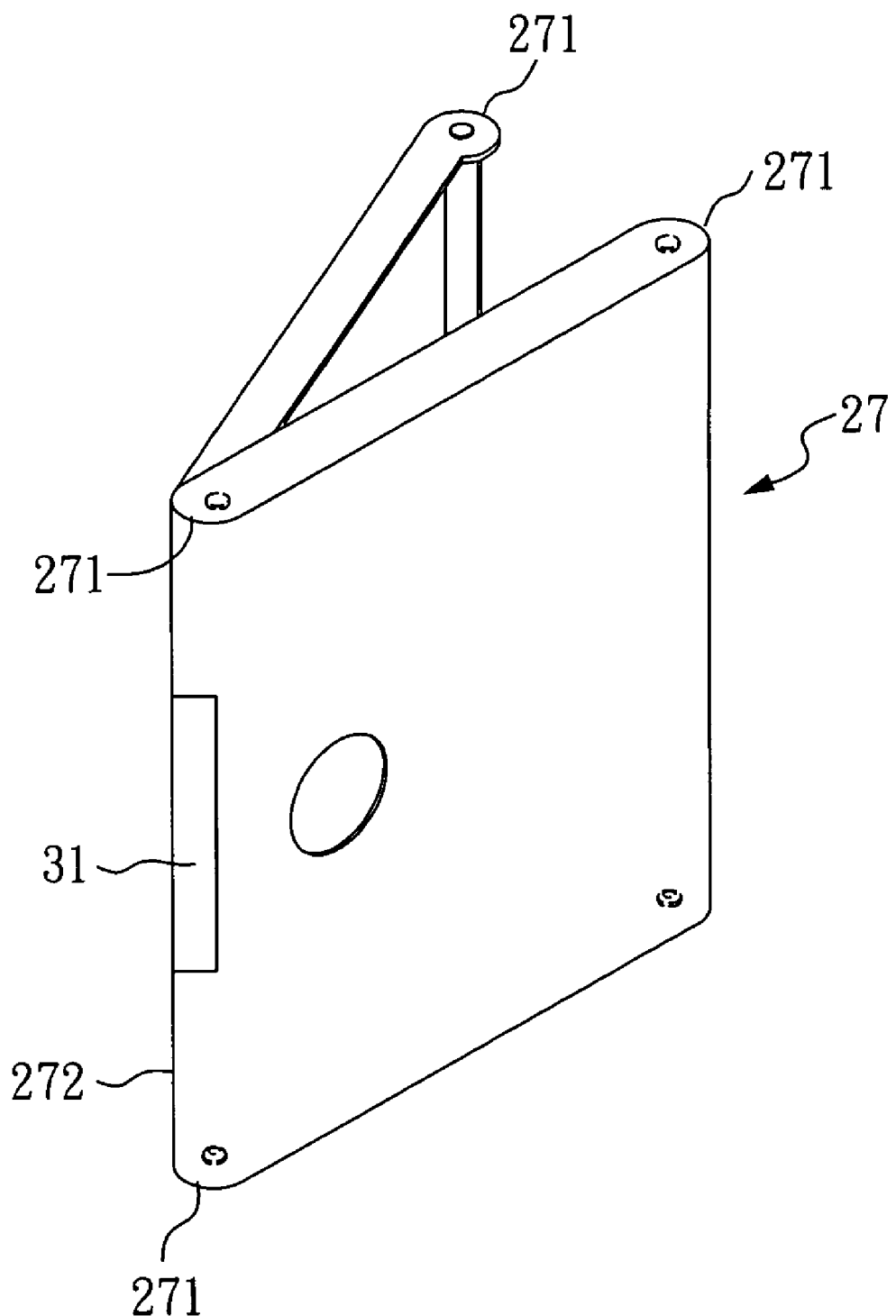
FIG. 8 is a perspective view illustrating a cartridge of the storage-access apparatus according to the present invention.

According to the present invention, as shown in FIG. 8, a perspective view illustrating a cartridge of the storage-access apparatus according to the present invention, the cartridge 27 is curved at edges 271, so that the actions of transfer can be undertaken smoothly. Further, the cartridge 27 is provided, at its pivotal edge 272, with an identification label 31, where the identification label 31 faces the first guiding portion 261 when laying the cartridge 27. As such, an optical-fiber lens or bar-code reader can see through the first guiding portion 261 and recognize image of the identification label 31.

Figure 9:
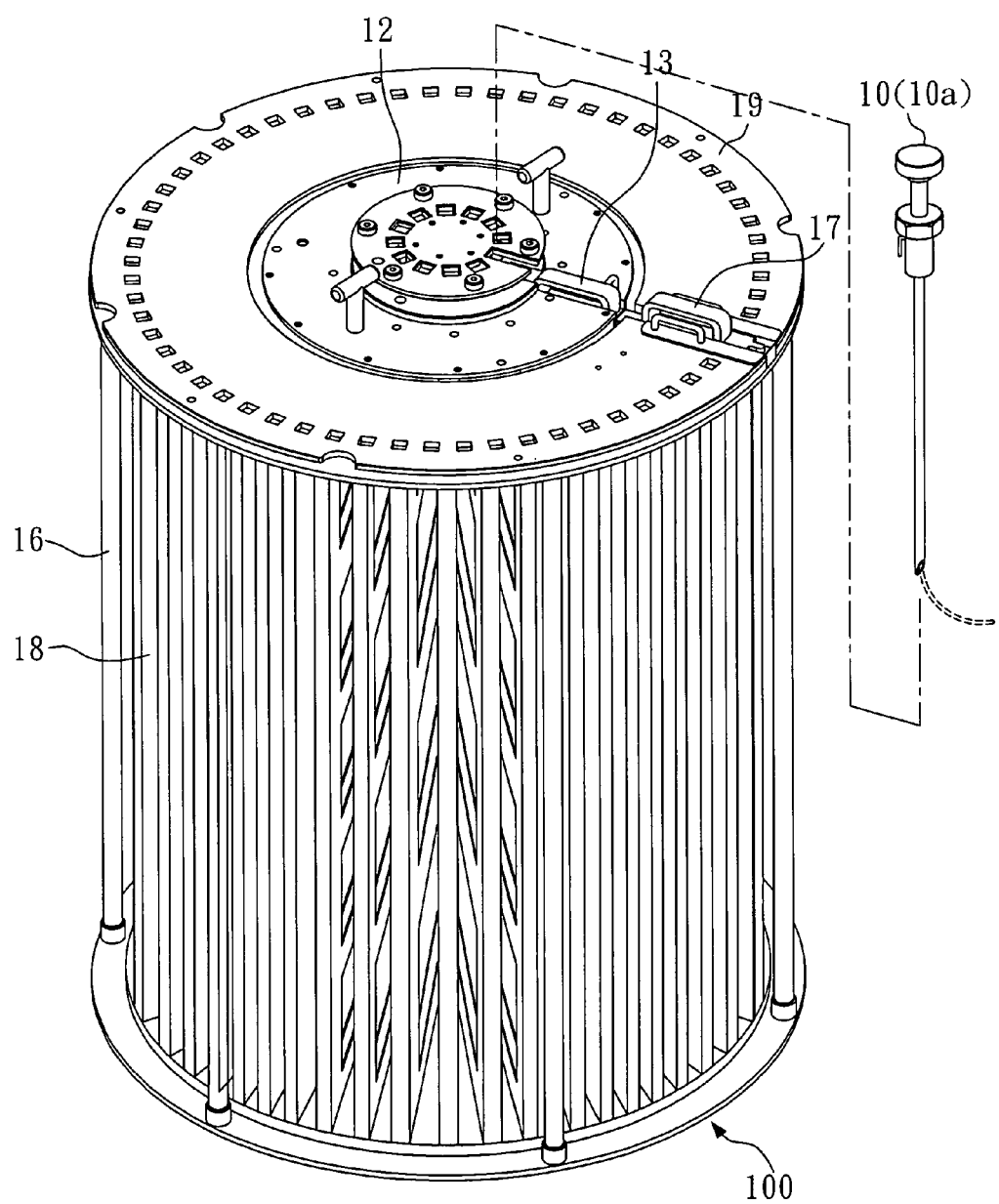
FIG. 9 is a perspective view, in outer appearance, illustrating the storage-access apparatus according to the present invention.

FIG. 9 is a perspective view, in outer appearance, illustrating the storage-access apparatus according to the present invention.

Figure 10:
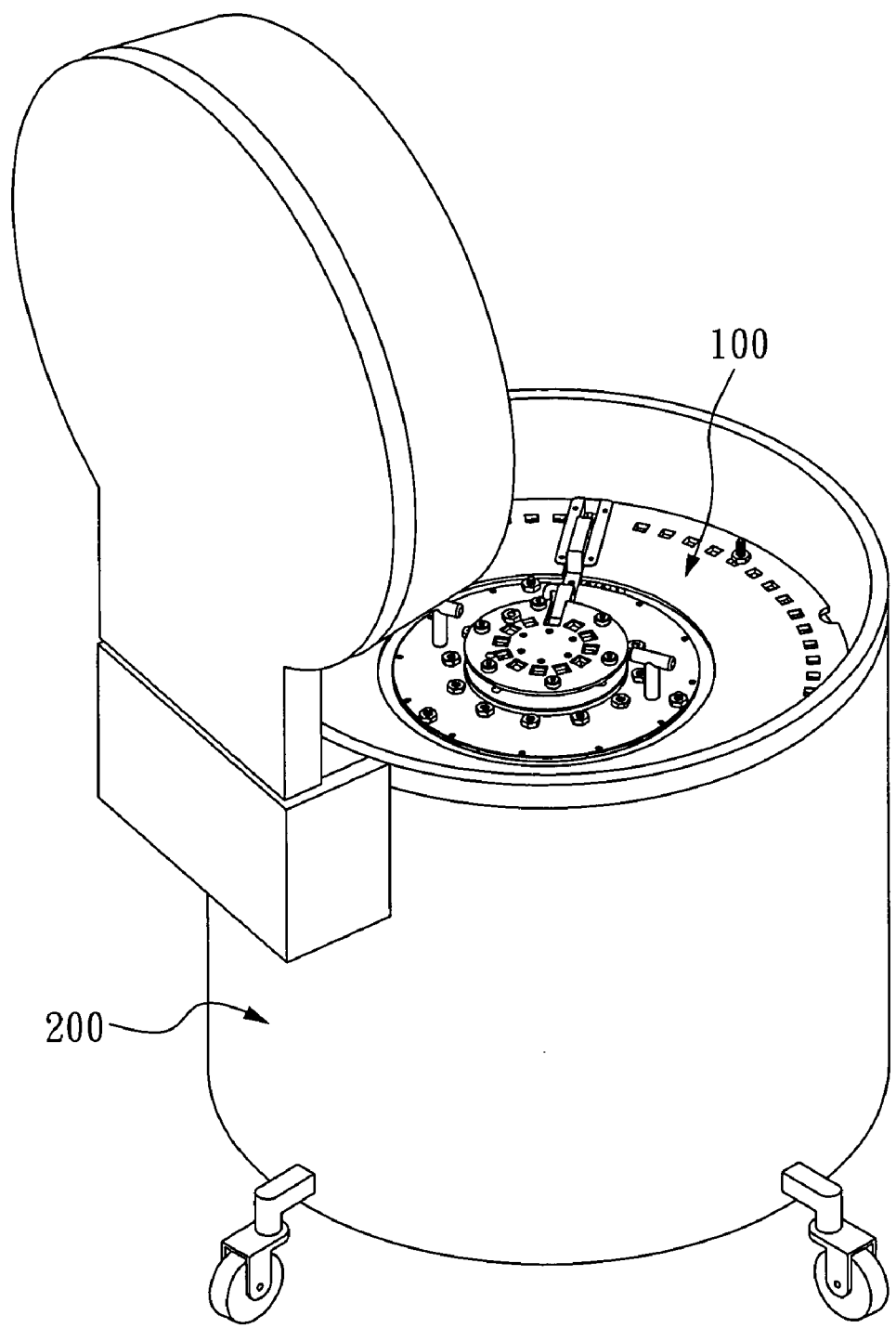
FIG. 10 is a perspective view illustrating a storage tank containing the storage-access apparatus according to the present invention.

Finally, as shown in FIG. 10, the storage-access apparatus 100 according to the present invention is disposed in a storage tank 200 filled with a liquid suitable for storing specimens (in the present invention, the liquid refers to liquid nitrogen), so that a storage system provided for storing specimens can be completed.

Although the present invention has been explained in relation to its preferred embodiments, it is to be understood that many other possible modifications and variations can be made without departing from the scope of the invention as hereinafter claimed.

What is claimed is:

1. A storage-access apparatus for storing a plurality of products, comprising:
    a first support device, including a first base;
    at least one first storage-access device, being supported on the first base and provided for depositing and picking up the products;
    at least one first storage device, being supported on the first base and provided for storing the products;
    a second support device, including a second base;
    at least one second storage-access device, being supported on the second base and provided for depositing and picking up the products;
    at least one second storage device, being supported on the second base and provided for storing the products; and
    a transporting device, being provided for transferring the products;
    wherein, the first storage-access device, the first storage device, the second storage-access device, and the second storage device each has an open side, a closed side opposite to the open side and a plurality of compartments between the open side and the closed side for receiving the products, and the transporting device is provided for transferring the products in the compartments, and the first storage-access device and the first storage device are arranged in a first circle, while the second storage-access device and the second storage device are arranged in a second circle such that the open sides of the first storage-access device and the first storage device in the first circle respectively face the open sides of the second storage device and the second storage-access device in the second circle, and the first storage-access device and the first storage device can rotate relative to the second storage-access device and the second storage device.

2. The storage-access apparatus as claimed in claim 1, wherein the first support device further includes a rotating unit connected with the first storage-access device and the first storage device, and the first storage-access device and the first storage device are positioned between the rotating unit and the first base.

3. The storage-access apparatus as claimed in claim 2, wherein the rotating unit is disposed at top or bottom of the storage-access apparatus.

4. The storage-access apparatus as claimed in claim 1, wherein the first base has a plurality of first positioning portions, corresponding to locations of the first storage-access device and the first storage device, for anchoring bottoms of the first storage-access device and the first storage device.

5. The storage-access apparatus as claimed in claim 2, wherein the rotating unit includes a bearing disk, a first rotating element, and a second rotating element, and wherein the bearing disk is fixed to the second base, the first rotating element can rotate relative to the bearing disk, and the second rotating element is connected with the first rotating element.

6. The storage-access apparatus as claimed in claim 5, wherein the rotating unit further includes a plurality of first rods connected with the second rotating element and the first base.

7. The storage-access apparatus as claimed in claim 5, wherein the rotating unit further includes a plurality of rolling elements, interposed between the bearing disk and the first rotating element, and when the first rotating element is rotated, it will rotate together with the rolling elements.

8. The storage-access apparatus as claimed in claim 5, wherein the rotating unit further includes a plurality of positioning elements, interposed between the bearing disk and the first rotating element, so that the first rotating element can reach to a target position while the first rotating element stops rotating.

9. The storage-access apparatus as claimed in claim 5, wherein the rotating unit further includes at least one first guiding element which is connected with the second rotating element, and which corresponds to a location of the at least one first storage-access device, so that the first storage-access device, upon insertion, can be guided into an accurate position.

10. The storage-access apparatus as claimed in claim 1, wherein the second base has a plurality of second positioning portions, corresponding to locations of the second storage-access device and the second storage device, for anchoring bottoms of the second storage-access device and the second storage device.

11. The storage-access apparatus as claimed in claim 1, wherein the second support device further includes a supporting unit which is fixed to the second base, and the second storage-access device and the second storage device are interposed between the supporting unit and the second base.

12. The storage-access apparatus as claimed in claim 11, wherein the supporting unit includes at least one second guiding element which corresponds to the location on which the at least one second storage-access device is disposed, so that the at least one second storage-access device can be guided and accurately inserted thereinto.

13. The storage-access apparatus as claimed in claim 1, further comprising a cover plate covering the top of the apparatus.

14. The storage-access apparatus as claimed in claim 1, wherein the compartments are separated from one another by a plurality of partitions.

15. The storage-access apparatus as claimed in claim 14, wherein the partitions are curved at edges so as to facilitate smooth transfer of the products.

16. The storage-access apparatus as claimed in claim 1, wherein the transporting device refers to a plurality of push-rod units each including a casing having a leading piece and an elastic element disposed in the casing and extending out of the leading piece and into the compartments.

17. The storage-access apparatus as claimed in claim 16, wherein the compartments are each provided, at its closed side, with a through first guiding portion, such that the push-rod units can be put into the first guiding portions.

18. The storage-access apparatus as claimed in claim 1, further comprising a plurality of cartridges for containing the products, wherein the cartridges are arranged in the compartments.

19. The storage-access apparatus as claimed in claim 18, wherein the cartridges are curved at edges.

20. The storage-access apparatus as claimed in claim 18, wherein the cartridges are each provided, on surface, with an identification label.

21. The storage-access apparatus as claimed in claim 1, further comprising a partition element, corresponding to the open sides of the first storage-access device, the first storage device, the second storage-access device, and the second storage device, for preventing the products from falling out of the compartments.

22. The storage-access apparatus as claimed in claim 21, wherein a through second guiding portion is provided at the open side of each of the first storage-access device, the first storage device, the second storage-access device, and the second storage device for receiving the partition element.

23. A storage system provided for storing a plurality of products, comprising:
a storage tank;
a liquid, filling in the storage tank; and
a storage-access apparatus, being disposed in the storage tank;
wherein the storage tank keeps the liquid under a certain temperature suitable for storing the products, and the storage-access apparatus comprises:
a first support device, including a first base;
at least one first storage-access device, being supported on the first base and provided for depositing and picking up the products;
at least one first storage device, being supported on the first base and provided for storing the products;
a second support device, including a second base;
at least one second storage-access device, being supported on the second base and provided for depositing and picking up the products;
at least one second storage device, being supported on the second base and provided for storing the products; and
a transporting device, being provided for transferring the products;
wherein, the first storage-access device, the first storage device, the second storage-access device, and the second storage device each has an open side, a closed side opposite to the open side and a plurality of compartments between the open side and the closed side for receiving the products, and the transporting device is provided for transferring the products in the compartments, and the first storage-access device and the first storage device are arranged in a first circle, while the second storage-access device and the second storage device are arranged in a second circle such that the open sides of the first storage-access device and the first storage device in the first circle respectively face the open sides of the second storage device and the second storage-access device in the second circle, and the first storage-access device and the first storage device can rotate relative to the second storage-access device and the second storage device.

24. The storage system as claimed in claim 23, wherein the storage-access apparatus further comprises a cover plate covering the top of the storage-access apparatus.

25. The storage system as claimed in claim 23, wherein the storage-access apparatus further comprises a plurality of cartridges for containing the products, where the cartridges are arranged in the compartments.

26. The storage system as claimed in claim 23, wherein the transporting device refers to a plurality of push-rod units each including a casing having a leading piece and an elastic element disposed in the casing and extending out of the leading piece and into the compartments.

27. The storage system as claimed in claim 26, wherein the compartments are each provided, at its closed side, with a through first guiding portion, such that the push-rod units can be put into the first guiding portions.

28. The storage system as claimed in claim 27, further comprising a partition element, corresponding to the open sides of the first storage-access device, the first storage device, the second storage-access device, and the second storage device, for preventing the products from falling out of the compartments.

29. The storage system as claimed in claim 28, wherein a through second guiding portion is provided at the open side of each of the first storage-access device, the first storage device, the second storage-access device, and the second storage device for receiving the partition element.

30. A storage-access apparatus for storing a plurality of products, comprising:
a first support device, including a first base;
at least one first storage-access device, being supported on the first base, the first storage-access device having an open side and a closed side and a plurality of vertically aligned compartments defined between the open and closed sides for depositing and picking up the products;
at least one first storage device, being supported on the first base, the first storage device having an open side and a closed side and a plurality of vertically aligned compartments defined between the open and closed sides for storing the products;
a second support device, including a second base;

at least one second storage-access device, being supported on the second base, the first storage-access device having an open side and a closed side and a plurality of vertically aligned compartments defined between the open and closed sides for depositing and picking up the products;

at least one second storage device, being supported on the second base, the second storage device having an open side and a closed side and a plurality of vertically aligned compartments defined between the open and closed sides for storing the products; and a transporting device, being provided for transferring the products;

wherein the transporting device is provided for transferring the products in the compartments, and the first storage-access device and the first storage device are arranged in a first circle, while the second storage-access device and the second storage device are arranged in a second circle around said first circle such that the open sides of the first storage-access device and the first storage device in the first circle respectively face the open sides of the second storage device and the second storage-access device in the second circle, and the first storage-access device and the first storage device can rotate relative to the second storage-access device and the second storage device.

* * * * *